US00PP36158P2

(12) United States Plant Patent
Heuger

(10) Patent No.: US PP36,158 P2
(45) Date of Patent: Sep. 24, 2024

(54) ***HELLEBORUS* PLANT NAMED 'HG 1416'**

(50) Latin Name: ***Helleborus ericsmithii* X *Helleborus* x *hybridus***
Varietal Denomination: HG 1416

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/389,526

(22) Filed: Nov. 14, 2023

(51) Int. Cl.
*A01H 5/02* (2018.01)
*A01H 6/72* (2018.01)

(52) U.S. Cl.
USPC ..... Plt./439
CPC ..... *A01H 6/72* (2018.05)

(58) Field of Classification Search
USPC ..... Plt./263.1, 439
See application file for complete search history.

*Primary Examiner* — Karen M Redden
(74) *Attorney, Agent, or Firm* — C. Anne Whealy

(57) ABSTRACT

A new and distinct cultivar of *Helleborus* plant named 'HG 1416', characterized by its upright to somewhat outwardly spreading and mounded plant habit; moderately vigorous growth habit; dark green-colored leaflets with lighter green-colored venation; freely flowering habit; white to greenish white-colored flowers; and good garden performance.

1 Drawing Sheet

Figure 1:
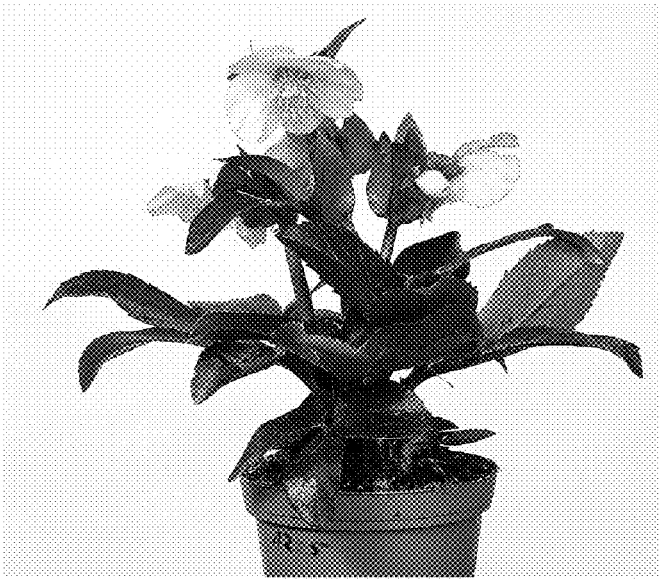

Botanical designation: *Helleborus ericsmithii* X *Helleborus* x *hybridus.*
Cultivar denomination: 'HG 1416'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Dec. 1, 2022, application number 2022/2740. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus ericsmithii* X *Helleborus* x *hybridus* and hereinafter referred to by the name 'HG 1416'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in December, 2015 of a proprietary selection of *Helleborus ericsmithii* identified as code number P842, not patented, as the female, or seed, parent and a proprietary selection of

*Helleborus* x *hybridus* identified as code number O1684, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in November, 2017.

Asexual reproduction of the new *Helleborus* plant by in vitro axillary meristem culture in a controlled environment in Glandorf, Germany since April, 2018 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HG 1416'. These characteristics in combination distinguish 'HG 1416' as a new and distinct *Helleborus* plant:

1. Upright to somewhat outwardly spreading and mounded plant habit.
2. Moderately vigorous growth habit.
3. Dark green-colored leaflets with lighter green-colored venation.
4. Freely flowering habit.
5. White to greenish white-colored flowers.
6. Good garden performance.

Plants of the new *Helleborus* differ from plants of the female parent selection in the following characteristics:

1. Plants of the new *Helleborus* are more compact than plants of the female parent selection.
2. Leaflets of plants of the new *Helleborus* are darker green in color than leaflets of plants of the female parent selection.

Plants of the new *Helleborus* differ from plants of the male parent selection in the following characteristics:

1. Leaflets of plants of the new *Helleborus* are darker green in color than leaflets of plants of the male parent selection.
2. Flowers of plants of the new *Helleborus* are lighter greenish white in color than flowers of plants of the male parent selection.

Plants of the new *Helleborus* can also be compared to plants of *Helleborus* x *ericsmithii* X *Helleborus* x *hybridus* 'COSEH 4100', disclosed in U.S. Plant Pat. No. 28,296. In side-by-side comparisons, plants of the new *Helleborus* differ primarily from plants of 'COSEH 4100' in flower color as flowers of plants of the new *Helleborus* are white to greenish white in color whereas flowers of plants of 'COSEH 4100' are red purple to greyed purple in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph at the top of the sheet (FIG. 1) is a side perspective view of a typical flowering plant of 'HG 1416' grown in a container.

Figure 2:
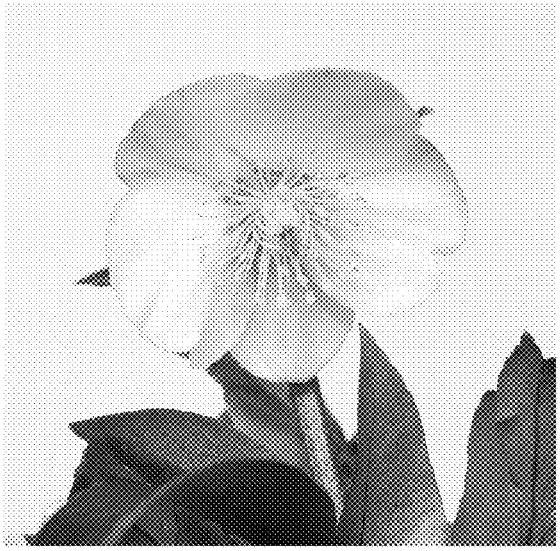

The photograph at the bottom of the sheet (FIG. 2) is a close-up view of a typical flowering plant of 'HG 1416'.

DETAILED BOTANICAL DESCRIPTION

The aforementioned photographs and following observations, measurements and values describe plants grown during the autumn in 13-cm containers in a glass-covered greenhouse in Glandorf, Germany and under cultural practices typical of commercial *Helleborus* production. During the production of the plants, day temperatures ranged from 12 C to 32 C and night temperatures ranged from 5 C to 12 C. Plants were 48 weeks old when the photographs were taken and 14 months old when the description was taken. In the following description, color references are made to The Royal Horticultural Society Colour Chart, 2015 Edition, except where general terms of ordinary dictionary significance are used.

Botanical classification: *Helleborus ericsmithii* X *Helleborus* x *hybridus* 'HG 1416'.

Parentage:

*Female, or seed, parent*.—Proprietary selection of *Helleborus ericsmithii* identified as code number P842, not patented.

*Male, or pollen, parent*.—Proprietary selection of *Helleborus* x *hybridus* identified as code number O1684, not patented.

Propagation:

*Type*.—In vitro axillary meristem culture.

*Time to initiate roots, winter*.—About 55 days at temperatures about 12 C.

*Time to produce a rooted young plant, winter*.—About 170 days at temperatures ranging from about 4 C to 15 C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held slightly above the foliar plane; plant shape, roughly flattened globular; moderately vigorous growth habit and slow growth rate.

*Plant height, soil level to top of foliar plane*.—About 12.3 cm.

*Plant height, soil level to top of flowers*.—About 21.5 cm.

*Plant diameter* (*area of spread*).—About 25.1 cm.

Leaf description:

*Arrangement*.—Leaves arranged in a basal rosette; leaves palmately compound with typically five, or occasionally three, leaflets per leaf.

*Leaf length*.—About 14.6 cm.

*Leaf width*.—About 17 cm.

*Leaflet length*.—About 10.7 cm.

*Leaflet width*.—About 5 cm.

*Leaf shape*.—Palmate; roughly reniform in outline.

*Leaflet shape*.—Elliptic to obovate to narrowly obovate.

*Leaflet apex*.—Acute.

*Leaflet base*.—Attenuate.

*Leaflet margin*.—Serrate to coarsely serrate; slightly to moderately coarsely undulate.

*Leaflet texture and luster, upper surface*.—Smooth, glabrous; coriaceous and tough; glossy.

*Leaflet texture and luster, lower surface*.—Smooth, glabrous; coriaceous and tough; moderately glossy.

*Leaflet venation pattern*.—Pinnate and reticulate.

*Leaflet color*.—Developing leaflets, upper surface: Slightly darker than a blend of NN137A and 147A; towards the base, close to 187A to 187D. Developing leaflets, lower surface: Close to 147B; midvein, close to 183A. Fully developed leaflets, upper surface: Darker than a blend of 147A and N189A; towards the base, close to 187A to 187B; venation, close to 144A. Fully developed leaflets, lower surface: Close to a blend of NN137C and 147B; venation, close to 199A.

*Petioles*.—Length: About 6.7 cm. Diameter: About 5 mm by 7 mm. Strength: Strong. Texture and luster, upper and lower surfaces: Smooth, glabrous; slightly glossy. Color, upper surface: Close to 146B; moderately covered with fine dots, close to 197C. Color, lower surface: Close to 146B; moderately to heavily covered with fine dots, close to 199B to 199C.

Flower description:

*Flower shape and habit*.—Single rotate bowl-shaped flowers arranged in panicles; freely flowering habit with about 7 to 18 flowers per inflorescence and about 60 flowers and flower buds per plant; flowers face mostly outwardly to slightly nodding.

*Fragrance*.—None detected.

*Natural flowering season*.—Plants begin flowering about ten months after planting; plants flower naturally during the late autumn into the winter in Germany.

*Flower longevity on the plant*.—About ten days; sepals persistent, other flower parts are not persistent.

*Flower buds*.—Length: About 2 cm. Diameter: About 1.4 cm. Shape: Ovate to elliptic. Texture and luster: Smooth, glabrous; slightly glossy. Color: Close to a blend of 150D and 157A.

*Inflorescence height* (*including peduncle*).—About 19.8 cm.

*Inflorescence diameter*.—About 12 cm.

*Flower diameter*.—About 7 cm.

*Flower depth*.—About 2.7 cm.

*Petals*.—All petals are transformed into nectaries.

*Sepals*.—Quantity and arrangement: About five, arranged in a single whorl. Length: About 3.6 cm. Width: About 3.5 cm. Shape: Broadly ovate to close to orbicular; slightly concave. Apex: Obtuse to broadly and bluntly acute. Base: Cuneate. Margin: Entire; slightly undulate. Texture and luster, upper surface: Smooth, glabrous; matte. Texture and luster, lower surface: Smooth, glabrous; matte to slightly glossy. Color: When opening, upper surface: Close to 155C, occasionally tinged with close to 145B; towards the base, close to 145C. When opening, lower surface: Close to 155C and 157D, occasionally tinged with close to 145B; towards the margins and apex, slightly tinged with close to 60C; at the base, close to 145B. Fully opened, upper surface: Close to NN155A and NN155B and 157C to 157D, occasionally tinged with close to 145A; towards the margins and apex, slightly tinged with close to 63B and 63C; at the base, close to 145B; venation, similar to lamina; color does not change with subsequent development. Fully opened, lower surface: Close to 155C and 157A to 157D, often tinged with close to 146D; towards the margins and apex, tinged with close to 186B and 186C; at the base, close to 145A; venation, similar to lamina; color does not change with subsequent development.

*Flower bracts*.—Quantity per flower: Typically one or two. Length: About 6.9 cm. Width: About 4.5 cm. Shape: Ovate to obovate. Apex: Acute to three-lobed. Base: Truncate to cuneate. Margin: Proximally, entire; distally, serrate; moderately coarsely undulate. Color, upper surface: Slightly darker than a blend of 139A and N189A; towards the base, close to 145A; midvein, occasionally tinged with close to N186C. Color, lower surface: Close to a blend of 146A and 147B; midvein, close to 183A and 183B.

*Peduncles*.—Length: About 13.9 cm. Diameter: About 7 mm to 9 mm. Aspect: About 10 degrees from vertical. Strength: Strong. Texture and luster: Smooth, glabrous; moderately glossy. Color: Close to 146D; heavily covered with fine dots, close to 187B and 187C.

*Pedicels*.—Length: About 2.9 cm. Diameter: About 3 mm. Aspect: About 15 degrees from peduncle axis. Strength: Moderately strong. Texture and luster: Smooth, glabrous; slightly glossy. Color: Lighter than 146D; heavily covered with fine dots, close to 178A and 178B.

*Reproductive organs*.—Stamens: Quantity per flower: About 60. Filament length: About 1.4 cm. Filament color: Close to 150D. Anther shape: Double and broadly reniform; basifixed. Anther size: About 2 mm by 3 mm. Anther color: Close to 150C. Pollen amount: Sparse. Pollen color: Close to 4D to lighter than 4D. Pistils: Quantity per flower: About five to seven. Pistil length: About 1 cm. Stigma diameter: About 0.3 mm. Stigma shape: Club-shaped. Stigma color: Close to 157D. Style length: About 9.5 mm. Style color: Close to 186C. Ovary color: Close to 150B. Nectaries (transformed petals): Quantity per flower: About 13 or 14. Length: About 9 mm. Diameter: About 3 mm. Shape: Tubular, flattened; apices, obtuse. Texture and luster, inner and outer surfaces: Smooth, glabrous; slightly glossy. Color, immature, inner and outer surfaces: Close to 144B; towards the apex, close to N144B. Color, mature, inner and outer surfaces: Close to 144B; towards the apex, close to 151C; with subsequent development, color becoming closer to 151A and towards the apex, close to 17B.

*Seeds and fruits*.—To date, seed and fruit development have not been observed on plants of the new *Helleborus*.

Garden performance: Plants of the new *Helleborus* have been observed to have good garden performance and to tolerate rain, wind, high temperatures about 35 C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HG 1416' as illustrated and described.

* * * * *